(12) United States Patent
Lentini et al.

(10) Patent No.: US 6,361,962 B1
(45) Date of Patent: Mar. 26, 2002

(54) TOXIN DETECTOR

(75) Inventors: David P. Lentini, San Francisco, CA (US); Vincent S. Camacho, Paris (FR)

(73) Assignee: Verseau Group, Wilmington, DE (US)

( * ) Notice: Subject to any disclaimer, the term of this patent is extended or adjusted under 35 U.S.C. 154(b) by 0 days.

(21) Appl. No.: 09/409,475

(22) Filed: Oct. 6, 1999

Related U.S. Application Data

(60) Provisional application No. 60/130,092, filed on Apr. 20, 1999, and provisional application No. 60/103,434, filed on Oct. 6, 1998.

(51) Int. Cl.[7] .............................. C12Q 1/02; C12Q 1/18; C12Q 1/22
(52) U.S. Cl. .............................. 435/29; 435/32; 435/31; 435/4; 435/283.1
(58) Field of Search .............................. 435/29, 32, 31, 435/4, 283.1; 422/50, 55

(56) References Cited

U.S. PATENT DOCUMENTS 5,306,466 A * 4/1994 Goldsmith .................... 422/55

* cited by examiner

*Primary Examiner*—Louise N. Leary
(74) *Attorney, Agent, or Firm*—David P. Lentini

(57) ABSTRACT

Methods, materials, and systems for detecting toxins are provided. In one aspect, a toxin contamination detector includes a substrate on which a bar code is printed. The bar code has a first color (e.g., black) that is effective to reflect light from a bar code scanning device to produce a bar code result. A toxin indicator is also included. The toxin indicator has a second color in the absence of toxin, which second color does not substantially affect or alter the bar code result. However, the toxin indicator presents a third color in the presence of toxin which substantially changes the bar code result; thereby indicating the presence of toxin.

22 Claims, 6 Drawing Sheets

TOXIN DETECTOR

CROSS REFERENCE TO RELATED APPLICATIONS

The present application is related to provisional U.S. patent application Ser. Nos. 60/103,434, filed Oct. 6, 1998; and 60/130,092, filed Apr. 20, 1999. Both of these provisional patent applications are incorporated herein by reference for all purposes.

BACKGROUND OF THE INVENTION

1. Field of the Invention

The present invention relates to immunoassays, and, more particularly, to the use of immunoassays to detect contaminants in foodstuffs. Still more particularly, the present invention provides an antibody detection system for detecting contaminants in packaged foodstuffs. The present invention has applications in toxicology, agriculture, and food safety.

2. The Related Art

The mass production and distribution of food, especially meat, poultry, and fish products, has contributed greatly to the good health enjoyed by most modern societies. In particular, the rise of industrial-scale meat, poultry, and fish processing and distribution allows even those living in very remote locations the opportunity to enjoy the nutritional and gastronomic benefits of a balanced diet. As a result, many childhood diseases associated with poor nutrition have all but disappeared from modern societies.

However, the mass production and distribution of food, and, more particularly, meat, has raised concerns. Changes in production and inspection of meat, poultry, fish processing and dining habits (modern societies tend to dine out more frequently) have lead to an increase in food contamination. The increase in the distribution and consumption of tainted food has been implicated in several outbreaks of food poisoning in recent years that have lead to numerous illnesses and deaths. Of particular concern has been the measured increase in meat contaminated with *E. coli* bacteria, especially the strain denoted 0157:H7. *E. coli* 0157:H7 produces a toxin that attacks the gastrointestinal tract causing severe cramping, abdominal pain, watery or bloody diarrhea, vomiting, and/or fever (Brody 1998). In some cases, the toxin can even cause kidney failure, which is fatal in about 30 percent of cases. Recently, the increase in *E. coli*-tainted meat has been attributed to the practice of raising cattle on high-grain diets that are known to provide more desirable meats (Diez-Gonzalez, Callaway et al. 1998).

In addition, other food-born toxins exist. Salmonella has been found increasingly in chicken and raw eggs. Listeria has been found in dairy products that have been improperly pasteurized. Ciguatoxins can be found in fish. These toxins are especially dangerous as they generally are not affected by cooking. Shell fish, such as oysters, mussels, and clams, often are contaminated with bacteria from waste water that is dumped in either untreated or partially treated form into coastal waters from which the shell fish are harvested. In addition, the increasing popularity of raw fish has also lead to increased incidents of food poisoning from contaminated fish. Moreover, recent outbreaks of "mad cow disease" have lead health officials to worry about the transmission of prion-based diseases from animals to man by the consumption of contaminated meat and/or meat products.

Often, the presence of dangerous bacteria is difficult for the consumer to detect. First, the amount of bacteria necessary to cause infection can be too small for detection by sight or smell. Second, the presence of contamination cannot be easily detected in packaging that blocks smells and hides most food surfaces. Thus, there is a need to provide consumers and distributors with an efficient, accurate means for detecting the presence of contaminants in food—especially packaged food. Ideally, such means for detecting food contaminants would be observable by the consumer or at the point of sale and inexpensive to provide.

One attempt to provide such a solution is described in U.S. Pat. No. 5,306,466 to Goldsmith and in U.S. Pat. No. 5,869,341 to Woodaman. These patents describe a bar code formed by depositing a known toxin in a "bar code" pattern on a substrate and ligating to the bound toxin a color-labeled anti-toxin to provide a visible bar code. The labeled toxin—anti-toxin substrate is located in a well set into the food container that collects juices and other moisture from the packaged food. Toxins in the juices compete with the bound toxin for the labeled anti-toxin. As more of the anti-toxin binds to the solution-borne toxin, the bar code is eroded leading to a detectable change in the label—either visually or by using a bar code reader which returns a "null" or "error" result upon scanning the eroded bar code. Unfortunately, such assays are complex and expensive to produce. Thus, the bar code described in the '466 and '3411 patents is not especially attractive for mass production of food packaging. Moreover, the bar code described in the '466 and '3411 patents cannot readily provide the identity of the toxin (or toxins) detected to a database when the bar code is scanned.

Thus, there remains a need for a highly scalable, accurate food contamination assay that can be readily perceived at various check points in the distribution chain and at the point of sale.

SUMMARY OF THE INVENTION

The present invention provides a food contamination assay that is accurate, easy to produce, and scalable. Thus, the present invention will be seen to provide a food contamination assay that can be mass produced for modern food packaging and distribution networks to provide produces, shippers, and consumers warning of food contamination.

In a first aspect, the present invention provides a toxin contamination detector. In one embodiment, the contamination detector of the invention includes a substrate on which a bar code is printed. The bar code has a first color (e.g., black) that is effective to reflect light from a bar code scanning device to produce a bar code result. A toxin indicator is also included. The toxin indicator has a second color in the absence of toxin, which second color does not substantially affect or alter the bar code result. However, the toxin indicator presents a third color in the presence of toxin which substantially changes the bar code result; thereby indicating the presence of toxin.

In one embodiment, the toxin indicator is deposited over the bar code so as to provide a background color against which the bar code is scanned or otherwise read. In another embodiment, the third color presented by the toxin indicator in the presence of toxin is effective to cause a "null" bar code result when the bar code is scanned. In a more particular embodiment, the toxin indicator comprises a polydiacetylene ("PDA") polymer coupled with a toxin-recognizing moiety. Still more specifically, the toxin indicator comprises a PDA-containing vesicle.

In another embodiment, the substrate is substantially transparent and the toxin indicator is deposited behind the substrate. In a still more particular embodiment, the toxin indicator is deposited to provide a second bar code result that is different from the first bar code result when the toxin indicator is exposed to toxin. In yet a more particular embodiment, the second bar code is effective to identify the toxin. The toxin indicator can be a PDA polymer or PDA-containing vesicle.

In as second aspect, the present invention provides a method for identifying toxin contamination in which a substrate having a first bar code printed thereon to produce a first bar code result is provided. A toxin indicator is provided proximate to the first bar code. The toxin indicator has a second color in the absence of toxin, which second color does not substantially affect or alter the bar code result. However, the toxin indicator presents a third color in the presence of toxin which substantially changes the bar code result; thereby indicating the presence of toxin. The toxin indicator is exposed to the toxin to change color from the second color to the third color. The bar code is then scanned to detect the presence of the toxin. Alternatively, the toxin indicator can be deposited to provide a second bar code.

In one embodiment, the result of the scan is stored in a database. In another embodiment, the toxin indicator is coupled with the first bar code to provide a "null" or "error" result when the bar code is scanned. In still another embodiment, the toxin indicator provides a background color for the first bar code.

These and other aspects and advantages will become apparent when the Description below is read in conjunction with the accompanying Drawings.

BRIEF DESCRIPTION OF THE DRAWINGS

FIG. 1A is a top view of the packaged foodstuff. FIG. 1B is a bottom view of the packaged foodstuff.

FIG. 4A illustrates the bar code prior to contact with a toxin. FIG. 4B illustrates the bar code following contact with the toxin.

FIG. 5A illustrates the detector prior to contact with a toxin. FIG. 5B illustrates the detector following contact with the toxin.

DESCRIPTION OF SOME EMBODIMENTS OF THE INVENTION

The present invention provides methods, materials, and systems to detect the presence of toxin contaminants. More particularly, the present invention provides toxin contaminant detectors that include calorimetric, immunoreactive polymers configured to detect and report the presence of toxin contaminants in conjunction with a bar code. In some embodiments, the calorimetric, immunoreactive polymers are provided with a bar code such that, upon detection of a toxin, the colorimetric, immunoreactive polymers change from a first color to a second color to thereby obscure or otherwise change the appearance of the bar code. In other embodiments, the calorimetric, immunoreactive polymers are deposited in the form of a bar code that is not detectable by a bar code scanner until the described color change occurs upon detection of a toxin. In still other embodiments, the toxin detector of the invention includes a hub-and-spoke format that changes appearance upon detection of a toxin. Thus, the present invention will be seen to provide toxin-specific information upon reaction with a toxin.

Figure 1A:
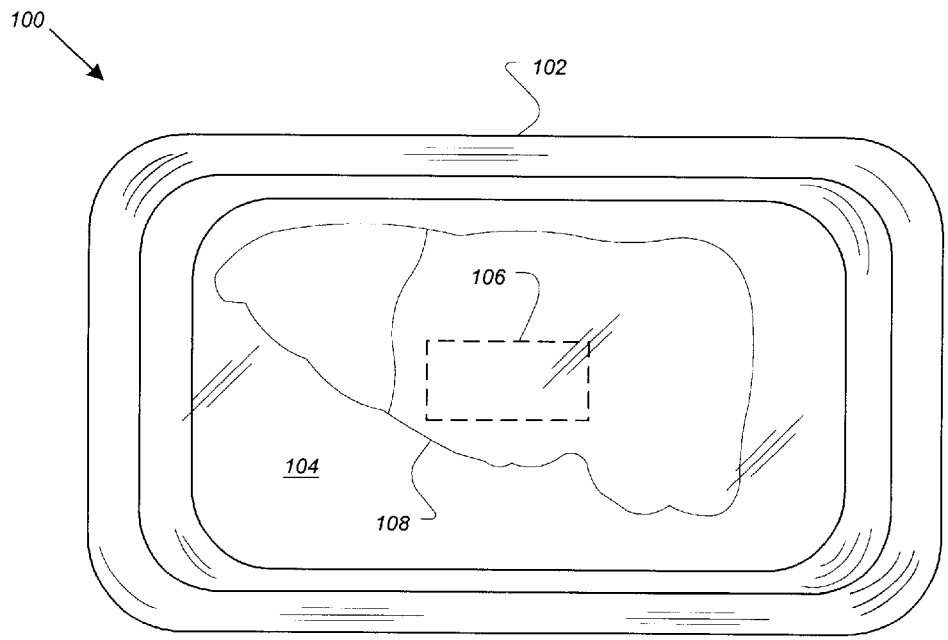
FIGS. 1A and 1B show two views of a packaged foodstuff in accordance with one embodiment of the present invention.

FIG. 1A shows a top view one embodiment of a food container in accordance with a first aspect of the invention at 100. Container 100 includes a tray 102 defining a tray interior 104 within which is a collector 106 that will be described in greater detail hereinbelow. Stored within tray interior 104 is a foodstuff 108. The design, materials, and construction of container 100 are known to those of skill in the container arts. The choice of design, materials, and construction will depend of factors such as, but not limited to, the materials to be held in the container as well as the conditions under which the container will be shipped and stored. In one embodiment, the container is a foodstuff container, and, more particularly, a container for holding meat, poultry, or fish for public sale and consumption. Often such containers are enclosed in a clear, colorless wrapping, such as formed from a plastic such as polyethylene.

Figure 1B:
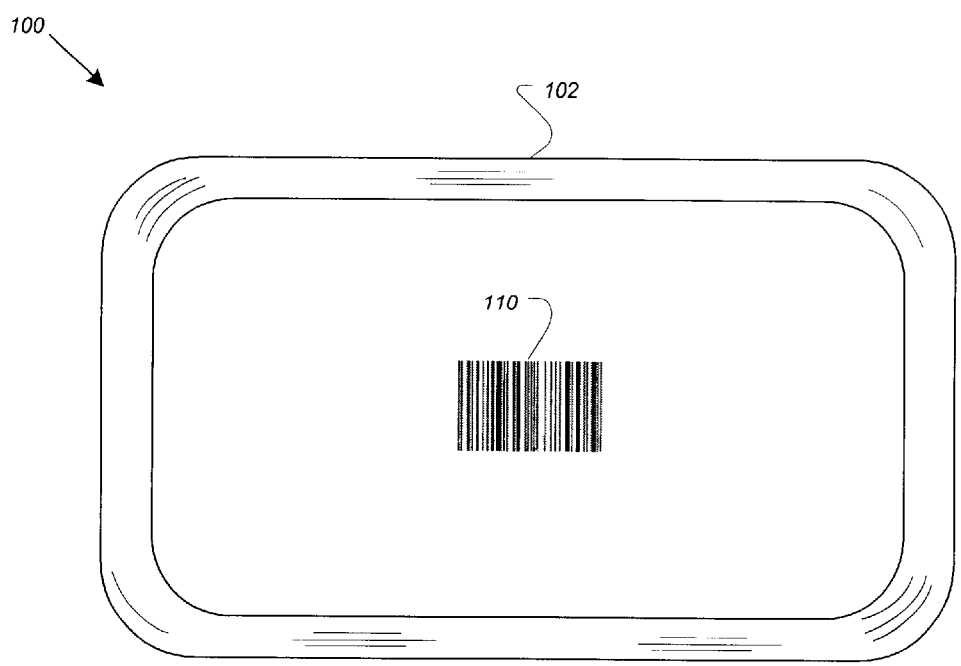
Figure 2:
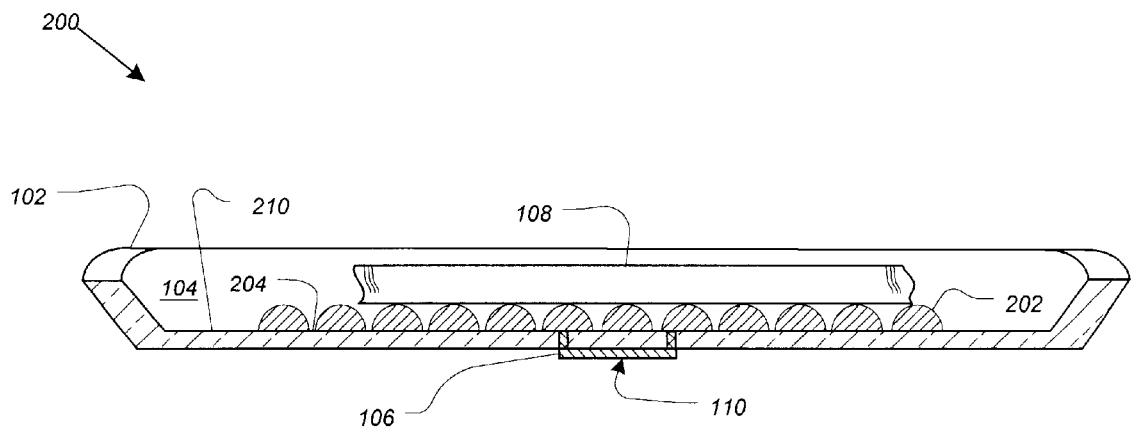
FIG. 2 is a cut-away view of packaged foodstuff in accordance with one embodiment of the present invention as illustrated in FIGS. 1A and 1B.

The bottom view of container 100 is shown in FIG. 1B. According to one embodiment of the invention, the bottom of container 100 includes a view of a bar code 110. As described in greater detail hereinbelow, bar code 110 is configured to provide a detectable indication of the presence of one or more toxin contaminants within container 100. Referring to FIG. 2, which provides a cut-away view of container 100, bar code 110 is arranged at the bottom of collector 106 that is arranged substantially below foodstuff 108. Collector 106 is configured to admit and substantially retain moisture, especially juices emitted by foodstuff 108, that are deposited at the bottom of container 100. Tray 104 can further include channels 204, such as those defined by ridge elements 202, to facilitate the collection of moisture in collector 106.

Figure 3:
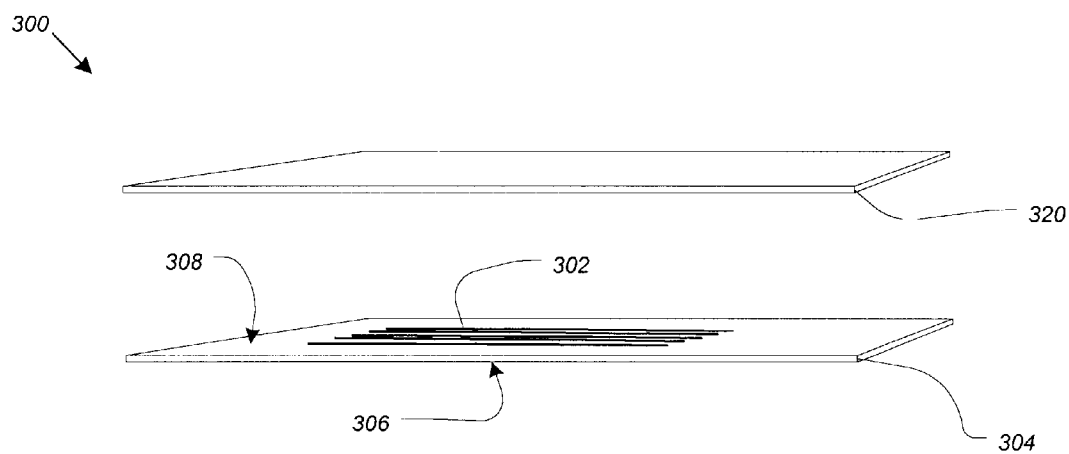
FIG. 3 is an illustration of a bar code in accordance with one embodiment of the present invention.

One embodiment of bar code 110 is illustrated at 300 in FIG. 3. There, bar code elements 302 are deposited on a substrate 304. Substrate 304 has inner and outer surfaces 306 and 308 respectively. The bar code elements 302 are formed from thin-film deposits of polydivinylacetylene ("PDA") that includes a receptor moiety specific for a toxin. Such films have been found to provide a colorimetric change upon exposure to the appropriate toxin (Charych, Nagy et al. 1993; Reichert, Nagy et al. 1995; Charych, Cheng et al. 1996; Okada, Peng et al. 1998). In general, substituted PDA can be formed from diacetylenes as illustrated below using known organic chemical techniques.

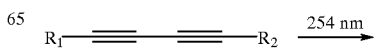

-continued

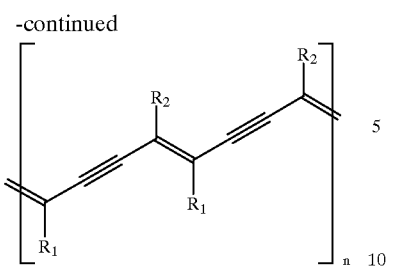

The resulting polymers are colored, typically a deep blue, presumably due at least in part to eneyne conjugation (Okada, Peng et al. 1998), although the actual mechanism of action is not important to the present invention. Moreover, it has been observed that PDAs including ligands for biological toxins undergo color changes upon exposure of the PDA to the corresponding toxin. For example, reaction of Compound 1 with influenza virus has been shown to cause a blue-to-red color change.

Compound 1

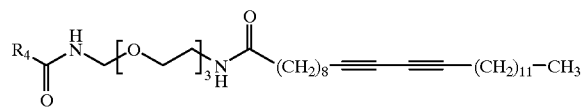

Where $R_4$ is the moiety shown below (Compound 2):

Compound 2

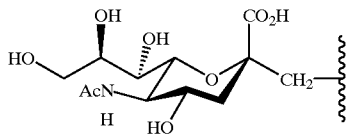

Other PDA derivatives have been shown to detect other toxins, including *E. coli* (Charych, Cheng et al. 1996). The color change is believed to be a general property of PDAs that arises from changes in effective conjugation length of the polydiacetylene backbone and alterations of side chain confirmation (Reichert, Nagy et al. 1995). Thus, the above-described color change is a general property of the interaction of PDAs bearing biological ligands with the corresponding toxin.

As noted above, the synthesis of the PDAs used in the present invention can be performed using methods, materials, and apparatus familiar to those of the skill in the organic chemistry arts. The ligands used to detect the toxin of interest can also be determined, synthesized, and coupled to the diacetylene using known materials and methods. Toxins of interest include, but are not limited to, *E. coli*, ciguatoxin, salmonella, botulism, listeria, scrape (or mad-cow disease), and other such harmful viruses and bacteria. Compounds effective to bind to prions can also be conjugated to the PDAs described herein to detect prion diseases. Examples of suitable polymer-ligand configureations are known to those of skill in the art (Charych, Nagy et al. 1993; Charych and Nagy 1997; Charych 1998).

Returning to FIG. 3, one embodiment of the present invention includes depositing a PDA in a bar code format on a substrate having a color substantially similar to the color displayed by the PDA upon exposure to the toxin. Thus, it will be appreciated that prior to exposure of the PDA to the corresponding toxin the bar code will appear against the background provided by the substrate in a contrast sufficient to enable scanning and decoding of the bar code using methods and apparatus known in the electronics arts. Upon exposure of the bar code to the toxin, the bar code changes color to substantially effectively impair scanning and decoding of the bar code. The resulting error thus warns of contamination. The warning can be confirmed by visual inspection of the color change in the bar code background.

For example, a first bar code is provided on the substrate in a first color along with the above-described toxin indicator PDA film, which, in the absence of toxin, has a second color that provides sufficient contrast with the bar code to enable the bar code to reflect light from a bar code reader to provide a bar code result (e.g., price and stock information). Upon exposure of the substrate to toxin, the PDA film undergoes a transition to a third color that substantially changes the bar code result. In one embodiment, the third color prevents decoding of the bar code to produce a null or error message as described above. This can be achieved in a variety of ways. For example, and without limitation, by depositing a thin film of the PDA over the entire substrate. Alternatively, the PDA can be deposited over a smaller area of the substrate that is sufficient to prevent decoding of the bar code. The PDA can even be deposited in a pattern such as a pictographic warning (e.g., a skull with crossed bones) or textual warning (for example, "DO NOT CONSUME").

Figure 4A:
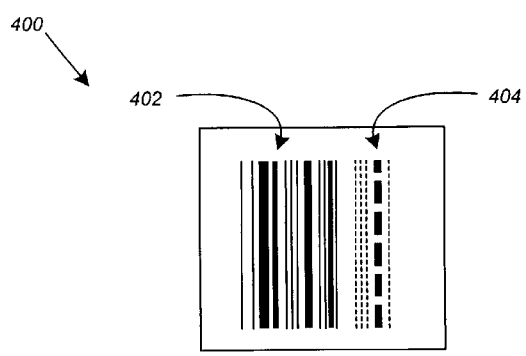
FIGS. 4A and 4B illustrate the operation of a bar code formatted toxin detector in accordance with one embodiment of the present invention.
Figure 4B:
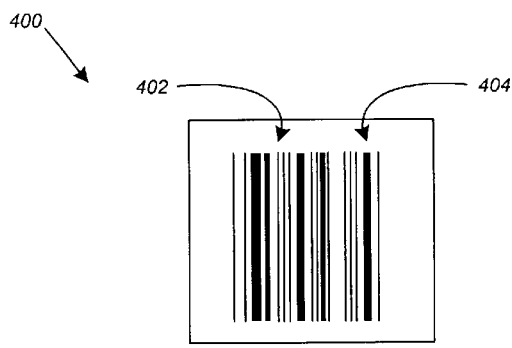

In another embodiment, the PDA is deposited in the form of a second bar code, and a filter (shown in FIG. 3 at 320) is provided to mask the presence of the second bar code until reaction of the PDA with toxin. Upon reaction with the toxin, the PDA changes color to provide sufficient contrast through the screen to allow the second bar code to be decoded along with the first bar code. In one example, illustrated in FIGS. 4A and 4B, the second bar code can append information to the first bar code. As shown at 400 in FIG. 4A, a printed bar code is provided at 402 with a non-decodable PDA bar code provided at 404. Upon exposure to toxin, however, PDA bar code 404 changes color to become decodable (see FIG. 4B). In a second example, the second bar code can provide information distinct from the information provided by the first bar code. Examples of such information include, but are not limited to, the identity of the toxin and the identity of the container's point of origin.

Figure 5A:
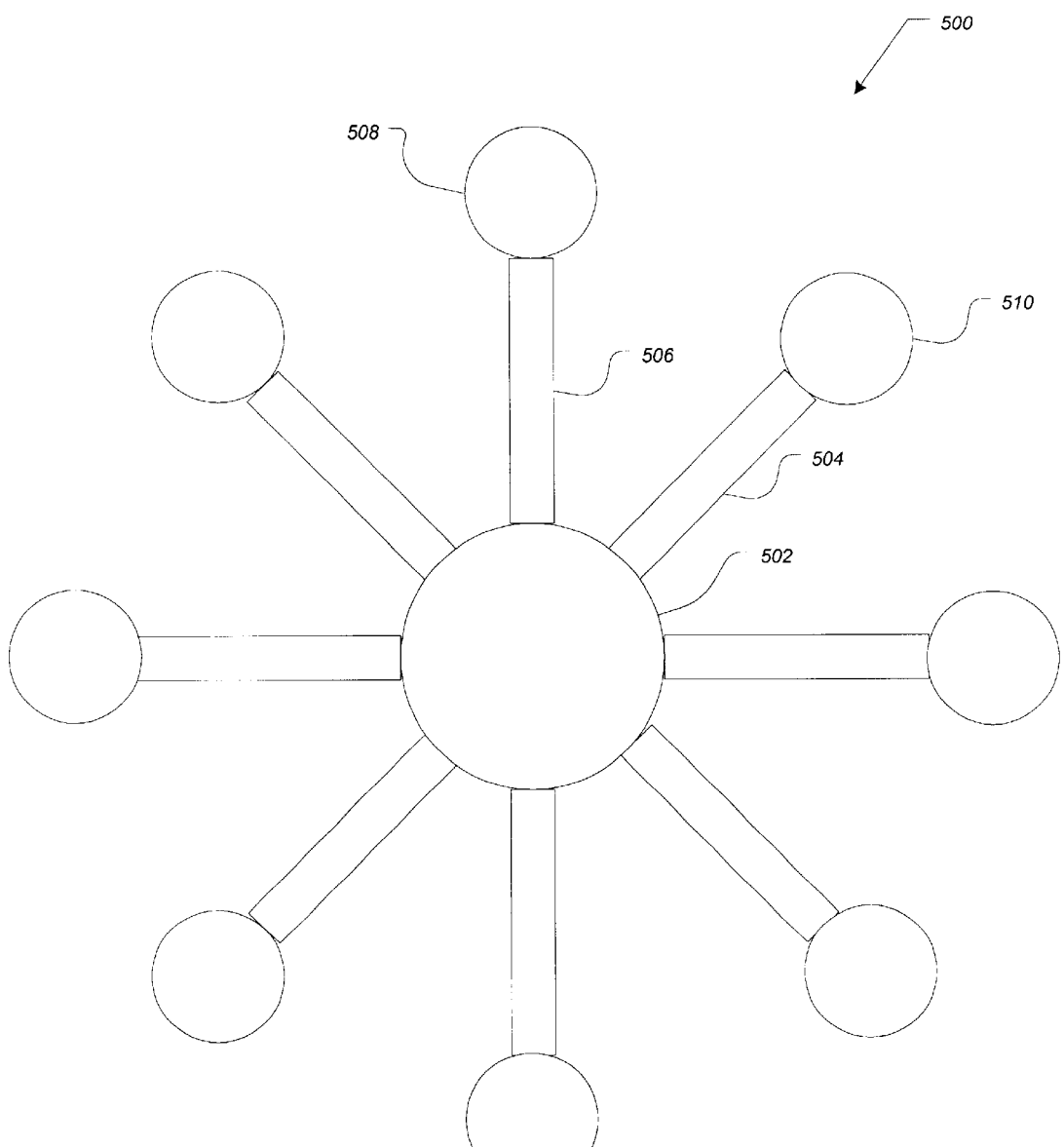
FIGS. 5A and 5B illustrate the operation of a hub-and-spoke formatted toxin detector in accordance one embodiment of with the present invention.
Figure 5B:
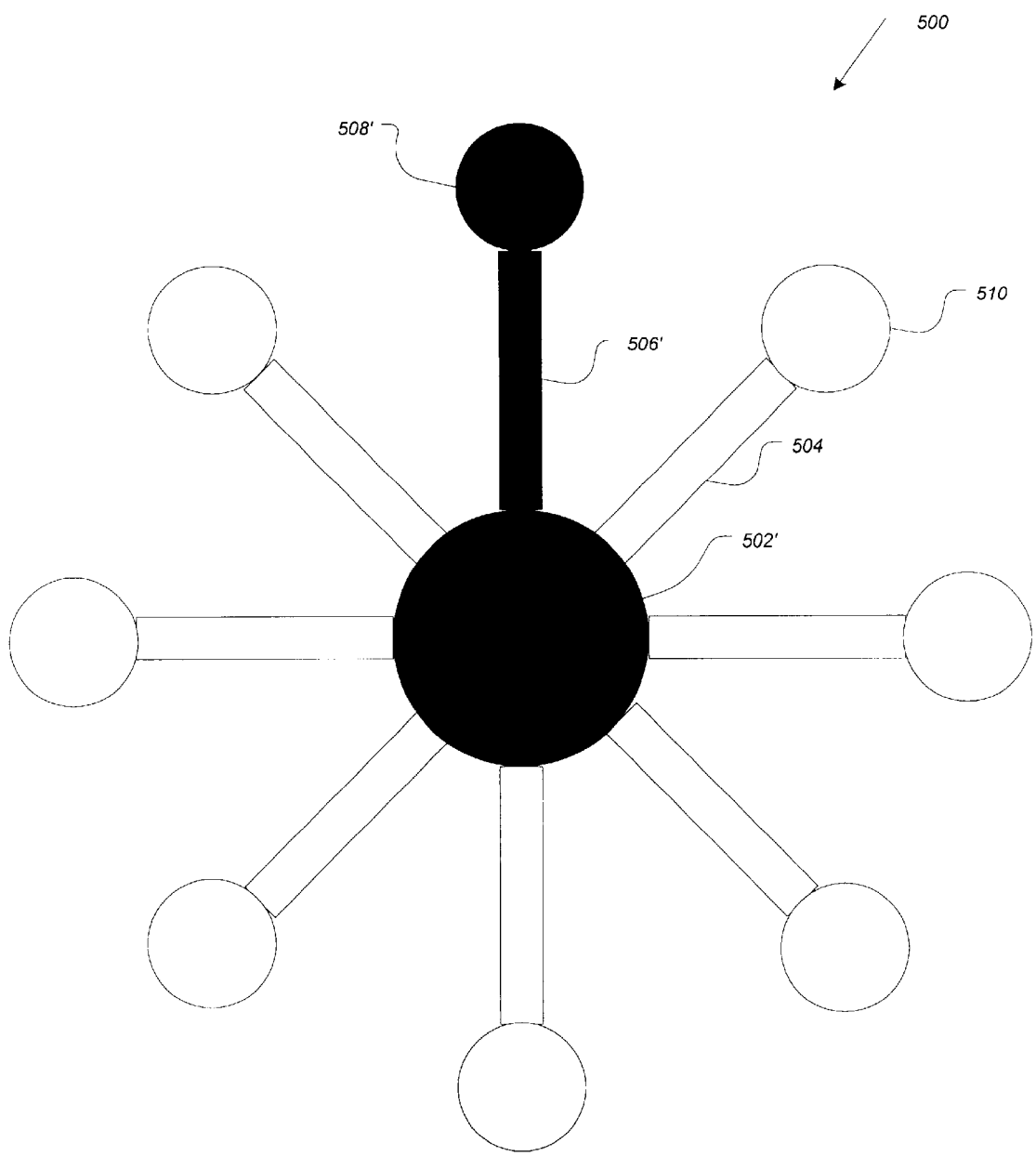

In another embodiment, the toxin detector of the invention is formatted in a hub-and-spoke configuration such as shown at 500 in FIGS. 5A and 5B. One example of a hub-and-spoke detector includes a central portion 502. Rectangular portions, such as shown at 504 and 506, extend radially outwardly from central portion 502. Each of the extending portions terminates at a distal portion as shown at 508 and 510. In one embodiment, each of the rectangular and distal portions comprises a PDA configured to respond to a particular toxin and central portion 502 is configured to respond to any toxin that can be detected by any of the rectangular and distal portions. Thus, as shown in FIG. 5A, in an "quiescent" state (i.e., a state in which no toxin has been detected) there is substantially no contrast between any of the elements of the detector. However, upon detection of a toxin the central portion as well as that rectangular and distal portion combination specific for the toxin change color (shown at 502', 506', and 508'), providing thereby a contrast pattern such as shown in FIG. 5B. Thus, a user can be warned of the presence of a toxin as well as the identity of the toxin by the emergence of a distinctive color/spatial pattern. Such a pattern can also be detected electronically, for example by using a modified contrast-sensitive scanner.

Alternatively, the central portion 502 can be a constant color designed to draw the user's eye to the detector to increase the likelihood of the user observing the status of the toxin detector. Alternatively, the central portion can be omitted. In still another alternative, the detector can comprises a series of arcuate regions arranged to form a circle. The appearance of a color change by one or more arcuate regions signals the presence and identity of a toxin. In yet other embodiments, the detector regions can be formed on other shapes such as rectangular strips. Even more arrangements will be apparent to those of skill in the art.

The above-described hub-and-spoke configuration can be applied and used with packaging as described for the bar code embodiment. In addition, both configurations can be used with other packaging such as bottles (glass or plastic, colored or uncolored), plastic containers including fruit and produce containers as well as polymer-based containers such as Styrofoam, or paper- or other fiber-based containers such as egg cartons. Furthermore, the toxin detector of the invention can be used inside container seals, such as bottle caps. Thus, the toxin detectors of the invention can be used to detect the presence of pathogens in foods such as milk, juice, yogurt, meat, fish, produce (e.g., lettuce, alfalfa sprouts, radishes), and fruit (e.g., strawberries, grapes, melons). In particular, the toxin detectors of the invention will be recognized as useful for detecting pathogens in foods derived from environments where manure is used for fertilization.

In a fourth embodiment, the toxin indicator is a PDA provided in the form of vesicles. The formation of PDA vesicles can be achieved using known methods and materials (Charych, Cheng et al. 1996). The color of the vesicle is a function of the chemical structure of the PDA; thus, the vesicle color can be "tuned" to provide various hues including blue, purple, orange, black, and red (Okada, Peng et al. 1998). The vesicles can be bound to the substrate using known methods to provide the background and bar codes described above. By choosing the appropriate PDA structure using known methods and materials, the color provided by the toxin indicator PDA can be selected to optimize detector function. Alternatively, the vesicles can be placed in the collector, either bound to one or more surfaces thereof or freely. In the latter embodiment, a semi-permeable membrane can be used to retain the free-floating vesicles in the collector but allow the influx of toxin. Still other arrangements will be apparent to those of skill in the art.

In addition, the detectors described herein can include more than one toxin contaminant. For example, one PDA can be directed to *E. coli,* another directed to salmonella, and a third directed to cholera. The PDAs can be constructed to provide different colors, and using the principles described above, can thus provide specific warning and identification of multiple toxins using a single detector (e.g., by using multiple screens). Furthermore, the intensity of the color change is generally related to the concentration (or amount) of toxin. Thus, the detector of the present invention can also provide an indication of the degree of contamination present in the container.

Figure 6:
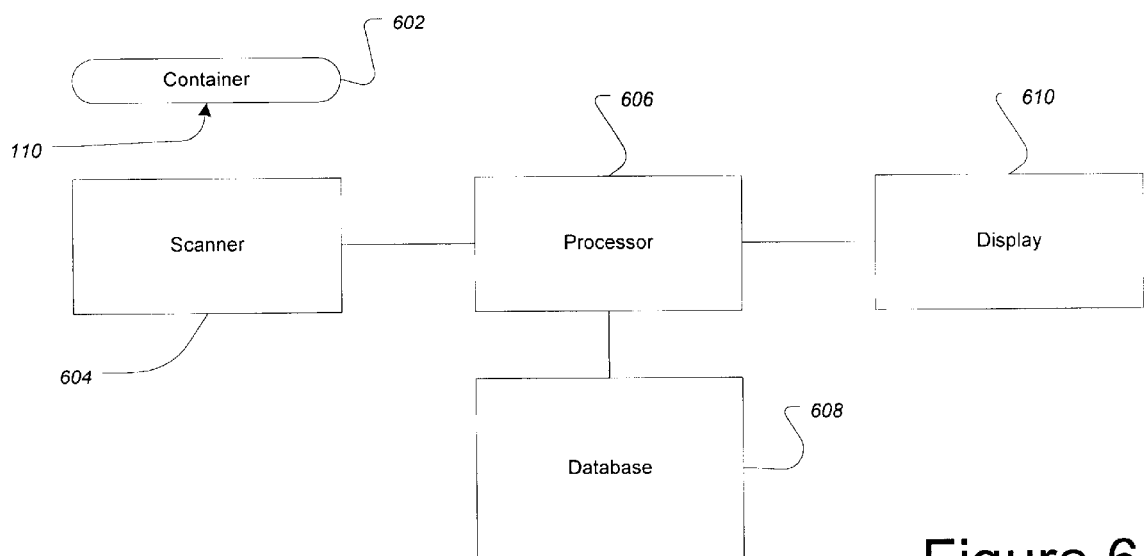
FIG. 6 illustrates the operation of the bar code on the invention at a point of sale location.

The use of the contamination detector of the invention is illustrated at 600 in FIG. 6. There, a container 602 is placed proximate to a bar code scanner 604 to allow scanning of the bar code in accordance with the present invention as described by the examples herein. Signals from scanner 604 are sent to a processor 606 for preprocessing and decoding. Information from processor 606 is sent to database 608 and display 610. Upon scanning and decoding, any error—either the failure to decode the bar code or the augmentation of the bar code—will signal to the operator that further inspection of the package is required. The presence of a color change serves to confirm the detection of a toxin in the package. The package can then be set aside for disposal or further analysis. The methods and materials for performing these functions will be apparent to those of skill in the electronics and computer science arts.

Generally, the scanning and decoding of a bar code depends at least in part on the detection of the contrast between the lines of the bar code against the background color. Thus, greater contrast provides greater reliability of decoding. Nevertheless, those of skill in the art of bioassays and electronics will appreciate that sufficient contrast can be achieved by manipulating various parameters using well-known methods and materials. For example, the concentration of the PDA (either in thin film or vesicle form) can be varied to provide sufficient contrast. Alternatively, other pigmenting agents can be used to "lighten" any background color provided by the PDA. These techniques can be used alone or in combination with signal preprocessing (e.g., baseline shifting) to allow accurate and rapid bar code scanning and decoding under the conditions provided by the bar code/toxin indicator combination.

In another embodiment, the present invention provides methods, compositions for detection toxins in which one or more of the above-described toxin detecting PDAs is combined in an aerosol which is sprayed in a volume of air and/or on a surface which may contain one or more toxins. The formation of such an embodiment can be accomplished using known methods and materials. Such an embodiment can be used to detect air-born toxins, and, more particularly, air-born pathogens such as anthrax. However, it will be appreciated such an aerosol detection embodiment can be used to detect any substance that can be identified using an antibody, such as certain chemicals. Thus, the present invention will be seen to have applications in the areas of chemical/biological warfare defense and chemical contamination detection. In one embodiment of such an application, an aerosol formulation of the toxin detector comprising one or more of the above-described vesicles is sprayed into a volume of air at a concentration effective to provide a detectable colored suspension of air-born vesicles. A change of color or a color indicating recognition of a toxin in the suspension indicates the presence of air-born toxins. By determining the concentration of vesicles and the color intensity as a function of concentration, an estimate can be provided as to the concentration of toxin present in the volume of air. Furthermore, mixtures of vesicles specific for different toxins and having different toxin recognition colors can be used to provide identification of multiple toxins in a single application of aerosol.

Alternatively, the aerosol can be sprayed onto the surface that is suspected of harboring one or more toxins. This is accomplished using a vesicle or polymer solution as described herein that is sprayed, painted, or otherwise applied to the surface. Methods and materials for making and applying such solutions will be apparent to those of skill in the art. A color change or the presence of a color indicating toxin recognition indicates the presence of toxin. Knowledge of the solution's concentration and the intensity of color as a function of toxin concentration provides a quantitative indication of the degree of contamination. The solution can be removed by washing. Indeed, it will be appreciated that removal of the solution also serves as an indicator of the completeness of toxin removal from the surface. Such solutions can be used on surfaces such as food preparation surfaces, washroom surfaces, medical examination room surfaces, laboratory surfaces, as well as meat, poultry, and fish surfaces. The solution can be washed-off once the presence or absence of contamination is determined. Indeed, it will be appreciated that removal of the solution also serves as an indicator of the completeness of toxin removal from the surface. Furthermore, mixtures of vesicles specific for different toxins and having different toxin recognition colors can be used to provide identification of multiple toxins in a single application. In yet another alternative, the toxin-detecting vesicle or polymer materials described herein can be combined with a cleaning agent such that toxin detection can be performed when the cleaning agent is applied to a surface. Such a combination obviates the need for separate detection and cleaning operations. In still another embodiment, a vesicle or polymer solution as described herein that is sprayed, painted, or otherwise applied to the surface of grains or pelleted foodstuffs, such as animal feed, to detect toxins or other pathogens (e.g., aflatoxin). Alternatively, such solutions can be applied to the surfaces of fruits or vegetables to detect toxins or chemical contaminants such as pesticide residues. It will be appreciated that by controlling the concentration of reagents and materials detection limits can be at least approximately established such that contaminants present in concentrations above a defined level can be detected.

In still another embodiment, the toxin-detecting PDAs and vesicles of the invention are applied directly to the interior of a food container. For example, the above-described PDAs can be applied to any interior surface that contacts the food or moisture released by the food, such as meat or poultry juices. In one embodiment, the PDAs are applied as polymers or vesicles to the interior surface 210 of tray 102 (see FIG. 2). The detection of a color change indicates the presence of toxin. Alternatively, the PDA polymers or vesicles can be applied to the surface of an indicator liner placed inside the food container and arranged to contact the foodstuff or substance released by the foodstuff. In another alternative, the toxin detecting materials described herein can be affixed directly to the surface of the packing material, or be incorporated directly therein, to provide detection. For example, the toxin detecting materials described herein can be included over a region or substantially throughout the interior surface of, and/or the wrapping covering, tray 102 of FIG. 1 to provide substantially continuous detecting contact with the foodstuff and any juices thereof. Mixtures of vesicles specific for different toxins and having different toxin recognition colors can be applied to the surface to provide identification of multiple toxins.

Figure 7:
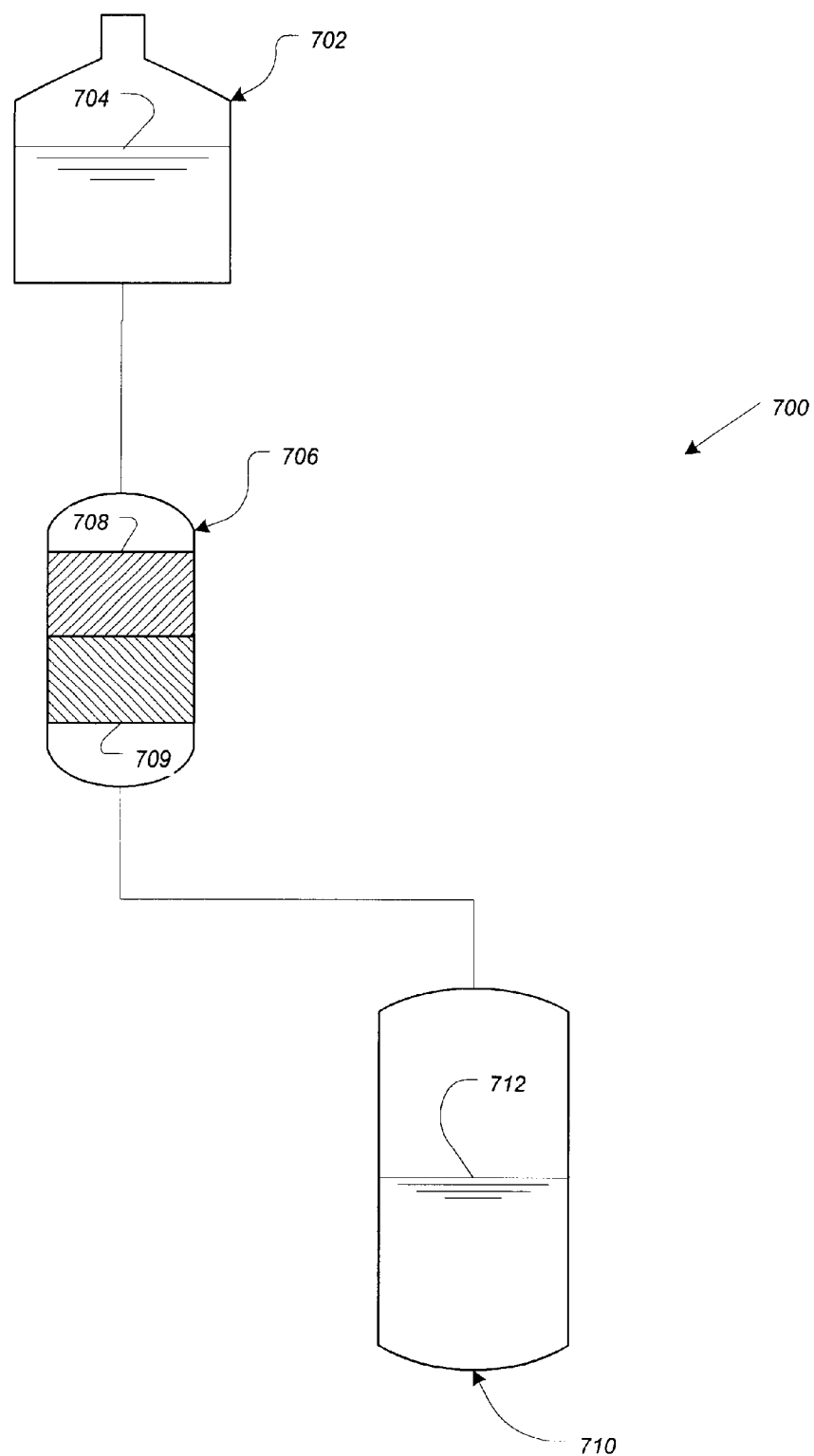
FIG. 7 illustrates the use of a toxin detector of the invention in combination with a purifier, such as a water purifier.

In another aspect, the toxin-detecting materials described herein can be used to determine the relative purity of liquids, such as water. Referring to FIG. 7 at 700, a first container 702 includes a liquid 704 (e.g., water) of questionable purity. The liquid from tank 702 is transferred to a purifier 706 that includes a purifier mechanism or material 708 and a toxin or contamination detector that includes the toxin-detecting materials described herein. In one embodiment, detector 709 includes toxin-detecting materials in a sol-gel matrix format as described in the art (Charych, Sasaki et al. 1999). The purified liquid 712 is stored in a second container 710. Alternatively, or in addition to this embodiment, the toxin-detecting materials can be included in either or both containers 702 and 710 by including a discrete detector that includes the toxin-detecting materials described herein or wherein the materials from which either or both containers are formed can include the toxin-detecting materials as described above. It will be further appreciated materials from which purifier 706 is formed can also include the toxin-detecting materials as described above.

In addition, the above-described embodiments adapted to provide identification of the pathogen or contaminant can be used in combination with the purifier described with reference to FIG. 7. For example, detector 709 can be arranged in a bar code or "wheel" format as described above so that the pathogen detected can be identified visually or with the aid of a scanning device. Such embodiments also include those for which a filter or colored material is included so that the bar code or wheel segment becomes visible or detectably changes upon recognition of a pathogen.

Thus, the present invention will be seen to provide a simple, reliable toxin contamination detector that is suitable for mass production. Using the toxin contamination detector of the invention, consumers, distributors, and producers can detect contaminants in packaged foodstuffs and other venues prior to their consumption or exposure to their effects; thus reducing the number of illnesses and deaths associated with the consumption of contaminated food or exposure to toxin.

Although certain embodiments and examples have been used to describe the present invention, it will be apparent to those having skill in the art that various changes can be made to those embodiment and/or examples without departing from the scope or spirit of the present invention. For example, it will be appreciated from the foregoing that various other colored polymers effective to change color in response to ligand binding can be used with the present invention, and that any ligand effective to bind to a toxin can be used in conjunction with the present invention. In addition, those of skill will appreciate that the toxin detector of the invention has widespread applications and can be used for detecting toxins under conditions other than those described herein. For example, the toxin indicator can be used to detect the presence of toxins in medicines, blood products, and medical samples.

Bibliography

The following references are incorporated herein by reference in their entirety and for all purposes.

Brody, J. (1998). *E. Coli Bacteria Can Be Eliminated From Cattle, Researchers Find. The New York Times.* New York.

Charych, D. (1998). *Polymeric Assemblies for Sensitive Colorimetric Assays.* PCT Patent No. WO 98/04743.

Charych, D., Q. Cheng, et al (1996). "A 'Litmus Test' for Molecular Recognition Using Artifical Membranes." *Chemistry & Biology* 3: 113–120.

Charych, D. and J. Nagy (1997). *Polymeric Film, Assay and Method for Direct Colorimetric Detection of Analytes.* PCT Patent No. WO 97/27316 Jan. 24, 1997.

Charych, D., J. O. Nagy, et al. (1993). "Direct Colorimetric Detection of a Receptor-Ligand Interaction by a Polymerized Bilayer Assembly." *Science* 261: 585–587.

Charych, D., D. Sasaki, et al. (1999). *Sol-Gel Matricies for Direct Colorimetric Detection of Analytes.* PCT Patent No. WO 99/10743 Aug. 31, 1998.

Diez-Gonzalez, F., T. R. Callaway, et al. (1998). "Grain Feeding and the Dissemination of Acid-Resistant *Escherichia coli* from Cattle." *Science* 281: 1666–1668.

Okada, S., S. Peng, et al. (1998). "Color and Chromism of Polydiacetylene Vesicles." *Acc. Chem. Res.* 31: 229–239.

Reichert, A., J. O. Nagy, et al. (1995). "Polydiacetylene Liposomes Functionalized with Sialic Acid Bind and Colorimetrically Detect Influenza Virus." *J. Am. Chem. Soc.* 117: 829–830.

What is claimed:

1. A toxin contamination detector, comprising:
   a. a substrate;
   b. a bar code printed on said substrate, said bar code having a first color effective to reflect light from a bar code scanning device to produce a bar code result; and
   c. a toxin indicator, said toxin indicator having a second color in the absence of a toxin which second color does not substantially alter said bar code result and a third color in the presence of said toxin that substantially changes said bar code result to indicate thereby the presence of said toxin.

2. The contamination in a test material detector of claim 1, wherein said toxin indicator is deposited on said substrate to provide a background for said bar code.

3. The contamination detector of claim 2, wherein said third color is effective to cause a null bar code result when said toxin indicator is exposed to said toxin.

4. The contamination detector of claim 3, wherein said toxin indicator comprises a polydiacetylene polymer coupled with a toxin-recognizing moiety.

5. The contamination detector of claim 4, wherein said toxin indicator comprises at least one polydiacetylene-containing vesicle.

6. The contamination detector of claim 5, wherein said vesicles are coupled with said substrate.

7. The contamination detector of claim 5, wherein said substrate is substantially transparent and said vesicles are deposited behind said substrate.

8. The contamination detector of claim 4, wherein said toxin-recognizing moiety is effective to recognize a toxin selected from the group consisting of: *E. coli,* Salmonella Sp., Listeria Sp., ciguatoxin and related marine polyethers, and aflatoxin.

9. The contamination detector of claim 1, wherein said toxin indicator is deposited on said substrate to provide a second bar code result different from said first bar code result when said toxin indicator is exposed to said toxin.

10. The contamination detector of claim 9, wherein said second bar code result is effective to identify said toxin.

11. The contamination detector of claim 10, wherein said toxin indicator comprises a polydiacetylene polymer coupled with a toxin-recognizing moiety.

12. The contamination detector of claim 11, wherein said toxin-recognizing moiety is effective to recognize a toxin selected from the group consisting of: *E. coli,* Salmonella Sp., Listeria Sp., ciguatoxin and related marine polyethers, and aflatoxin.

13. A method for identifying toxin contamination in a material, comprising the steps of:
   a. providing a substrate having a first bar code printed thereon which produces a first bar code result when said first bar code in scanned;
   b. providing a toxin indicator proximate to said first bar code, said toxin indicator having a second color in the absence of said toxin which second color does not substantially alter said bar code result and a third color in the presence of said toxin that substantially changes said bar code result to indicate thereby the presence of said toxin;
   c. exposing said toxin indicator to said toxin to cause thereby said toxin indicator to change from said second color to said third color; and
   d. scanning said first bar code to detect the presence of said toxin.

14. The method of claim 13, further including the step of storing the result from said scanning in a database.

15. The method of claim 13, wherein said step of providing a toxin indicator proximate to said first bar code comprises coupling said toxin indicator with said substrate to provide thereby a null or error result when said first bar code is scanned.

16. The method of claim 13, wherein said step of providing a toxin indicator proximate to said first bar code comprises arranging said toxin indicator to function as a background for said first bar code.

17. The method of claim 13, wherein step of providing a toxin indicator proximate to said first bar code comprises coupling said toxin indicator with said substrate to provide thereby a second bar code.

18. The method of claim 17, further comprising the step of scanning said second bar code.

19. The method of claim 18, further comprising the step of identifying said toxin from said second bar code.

20. A system for identifying a toxin contaminant, comprising:
   a. a container including a toxin contamination detector as described in claim 1;
   b. a scanner configured to scan said toxin contamination detector, said scanner being coupled with and configured to send signals to;
   c. a processor configured to process signals received from said detector, said processor being configured to process said signals to decode thereby bar code information;
   d. such that said scanner and said processor are effective to identify the presence of said toxin in said container upon scanning said toxin contamination detector.

21. A water purifier, comprising:
   a. an inlet adapted to receive water including one or more impurities;
   b. a purifier configured to remove at least a portion of said impurities; and
   c. a calorimetric detector configured to identify the presence of at least one of said impurities, said calorimetric detector comprising a detector of claim 1.

22. The purifier of claim 21, wherein said detector comprises a sol-gel matrix.

* * * * *